US005672356A

United States Patent [19]
Rault et al.

[11] Patent Number: 5,672,356
[45] Date of Patent: Sep. 30, 1997

[54] BIOADHESIVE PHARMACEUTICAL COMPOSITION FOR THE CONTROLLED RELEASE OF ACTIVE PRINCIPLES

[75] Inventors: Isabelle Rault, Saint Lye la Foret; Gérald Pichon, Orleans; Alain Cuine, Saint Jean de Braye, all of France

[73] Assignee: Adir et Compagnie, Courbevoie, France

[21] Appl. No.: 309,930

[22] Filed: Sep. 21, 1994

[30] Foreign Application Priority Data

Sep. 22, 1993 [FR] France .................... 93 11259

[51] Int. Cl.$^6$ ............ A61K 9/22; A61K 47/32; A61K 47/36
[52] U.S. Cl. ............ 424/468; 424/486; 424/488; 424/434; 424/435; 424/436; 514/960; 514/772.6; 514/778; 514/944; 252/315.3
[58] Field of Search ............ 424/485–86, 488, 424/434–436, 430, 468, 470; 514/944, 960, 772.6

[56] References Cited

U.S. PATENT DOCUMENTS

| | | | |
|---|---|---|---|
| 4,666,705 | 5/1987 | DeCrosta et al. | 424/470 |
| 4,755,386 | 7/1988 | Hsiao et al. | 424/435 |
| 4,772,470 | 9/1988 | Inoue et al. | 424/435 |
| 4,814,176 | 3/1989 | Makino et al. | 424/468 |
| 4,948,580 | 8/1990 | Browning | 424/434 |
| 5,032,384 | 7/1991 | Yeh et al. | 424/443 |
| 5,112,620 | 5/1992 | Repka et al. | 424/484 |
| 5,292,517 | 3/1994 | Chang | 424/486 |
| 5,330,761 | 7/1994 | Baichwal | 424/469 |
| 5,385,729 | 1/1995 | Prencipe et al. | 424/70.11 |

*Primary Examiner*—Edward J. Webman
*Attorney, Agent, or Firm*—The firm of Gordon W. Hueschen

[57] ABSTRACT

Bioadhesive pharmaceutical composition for the controlled release of active principles locally across the buccal cavity or systemically across a mucous membrane, wherein it is composed of an active principle, a compound (A), a compound (B) and excipients as defined in the description.

4 Claims, No Drawings

BIOADHESIVE PHARMACEUTICAL COMPOSITION FOR THE CONTROLLED RELEASE OF ACTIVE PRINCIPLES

The present invention relates to a new bioadhesive pharmaceutical composition which makes possible the controlled release of active principles locally across the buccal cavity or systemically across a buccal (cheek or gum), perlingual, nasal, vaginal or rectal mucous membrane. The pharmaceutical composition according to the invention provides for a more or less rapid release of the active principle and can remain fixed for a longer or shorter time to the buccal (cheek and gum), perlingual, nasal, vaginal, or a mucous membrane. Administration by the transmucosal route has the advantage, at the metabolic level, of avoiding the significant metabolization of the active principle by the effect of a first passage through the liver and thus, at the clinical level, of reducing the doses administered while improving the clinical effectiveness. The active principle does not undergo the various enzymatic or chemical degradations present throughout the length of the gastrointestinal tract or the disadvantages related to the function and to the physiology of the gastrointestinal system.

The possibilities of administration of an active principle across a mucous membrane depend on various factors. In particular, the composition must not detrimentally affect the tissue in any way following prolonged contact and must not cause irritations, allergies or sensitizations and the active principle must be able to cross a fairly small tissue surface at a diffusion rate which is sufficient to obtain plasma levels suited to the therapeutic requirements. A bioadhesive form has the property of adhering to a biological tissue, for example to a mucous membrane in the buccal cavity, and of being maintained there for a longer or shorter time. The bioadhesion phenomenon is described in the literature and is provided by the establishment of binding between one or more compounds of the pharmaceutical dosage form and functional chemical groups present at the surface of the biological tissue. The interactions involved in the bioadhesion mechanism are described as being physical, mechanical or chemical in nature.

The pharmaceutical composition according to the invention, in addition to the fact that it is new, makes it possible to obtain an intense bioadhesive effect and a controlled and reproducible release of the active principle.

The bioadhesive pharmaceutical composition of the present invention is composed of:

an active principle, a compound (A) comprising one or a number of copolymers formed by the copolymerization of methyl vinyl ether and of maleic anhydride (or its derivatives: acids, esters, or salts), a compound (B) comprising one or a number of compounds such as polyvinylpyrrolidone, polyvinyl alcohol, polyethylene glycol, alginic acid and derived alginates, cellulose and its derivatives such as, for example, ethyl cellulose, hydroxymethyl cellulose, hydroxypropyl methylcellulose, and the like, starches of various origins and their derivatives such as chemically modified maize starch, gum arabic, gum tragacanth, guar gum, xanthan gum, carob gum, carraghenates, a protein used alone or in combination with other compounds of biological origin, or cyclodextrins or derivatives such as β-cyclodextrins, hydroxypropyl-β-cyclodextrins or partially methylated β-cyclodextrins, and excipients acting as diluent, such as lactose or calcium dihydrogenphosphate, as binder or as lubricant, such as magnesium stearate or colloidal silica, to which can be added excipients acting as absorption promoters, as dye, as flavoring, as sweetener or as disintegrants.

Compound (A) comprises one or a number of copolymers selected from copolymers of methyl vinyl ether and of maleic anhydride or of its derivatives in the form of acids, esters or salts. These copolymers have the following formula:

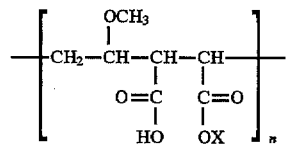

Specific examples of this type of copolymers currently commercially available are Gantrez® of AN, S, ES and MS type (GAF products):

Gantrez AN®=anhydride
Gantrez S®=acid, X=H
Gantrez ES®=ester, X=alkyl
Gantrez MS®=salt, X=Ca or Na The bioadhesion is provided mainly by Compound (A) and the prolonged release is provided by the combination of Compound (A) and of Compound (B). The proportion of Compound (A) is between 5 and 85 mass % and the proportion of Compound (B) is between 5 and 85 mass %. The bioadhesion and the prolonged release can be adjusted depending on the proportions used.

Compound (A) is preferentially a mixture of the sodium and calcium salts of the copolymer of methyl vinyl ether and of maleic anhydride (or its derivatives: acids, esters or salts). The amount of Compound (A) is preferentially between 10 and 30 mass %. Compound (B) is preferentially modified, i.e., acetylated, maize starch. The amount of Compound (B) is preferentially between 10 and 50mass %. The diluent can be lactose, calcium dihydrogenphosphate or other appropriate diluents.

The pharmaceutical composition according to the invention can be provided in the form of a tablet, a lozenge, a cream or a gel. A preferential form is the production of a tablet which can be prepared by mixing Compound (A), Compound (B), the active principle and excipients by wet granulation followed by a compression.

In the granulation process, the two polymers are used separately in the tablet by virtue of a novel manufacturing process which combines a granulated inner phase and a non-granulated outer phase. This process makes it possible to retain intact the bioadhesive properties of the starting polymer and reproducibly to control the bioadhesion and the release of the active principle.

This granulation process is composed of various successive stages:

The preparation of the inner phase is carried out by mixing the active principle with all or part of the amount of Compound (B), to which the diluent is added.

The mixture obtained is then granulated with a wetting liquid, preferentially water or water/alcohol mixtures.

The granule obtained is sieved and then dried at a temperature lying between 20° and 100° C. The granule is then graded by passing through a sieve.

The phase known as the outer phase is prepared in parallel. It is composed of the mixture of Compound (A) and Compound (B), if it has not been entirely introduced into the inner phase. The inner and outer phases are then mixed. The excipients defined as acting as lubricant, absorption promoters, flavoring, sweetener, dye and disintegrant are optionally added to this mixture. The whole is mixed and then graded by passing through a sieve.

The mixture obtained is compressed.

The choice of the shape and size of the tablet is important. These two criteria condition the desired release kinetics, influence the bioadhesion by modifying the contact surface between the mucous membrane and the pharmaceutical dosage form and finally make it pleasanter to place and maintain the tablet.

The pharmaceutical composition according to the invention can be provided in the form of a round tablet with a diameter of 3 to 15 mm and with a thickness of 1 to 5 mm. It can also be provided, for example, in the form of a tablet of chamfered round, oblong, semi-convex or any other geometric form having the advantage of providing for the better prolonged maintenance of the form, for example in the maxillogingival groove of the buccal cavity or under the tongue.

The pharmaceutical composition according to the invention is distinguished in that it is kept applied to the buccal, perlingual, nasal, rectal or vaginal mucous membrane for a period of time ranging from 10 minutes up to 12 hours.

Mention may be made, in a non-limiting way, among active principles which form part of the composition according to the invention, of antiinflammatory agents and analgesics, whether possessing local or systemic action, such as for example indomethacin, ibuprofen, diclofenac, tenoxicam or piroxicam, disinfectants such as chlorhexidine and the derived salts, enzymes, coronary vasodilators such as nitroglycerin or isosorbide dinitrate, antiasthmatics, antibacterials, antibiotics such as penicillin or erythromycin, cardiotonics such as digitalin, local anesthetics such as lidocaine, antianginals, antidysrhythmics, antihypertensives, aggregation inhibitors, antitussives and expectorants such as codeine phosphate, antihistamines such as chlorphenamine, steroidal antiinflammatories such as prednisolone, dopaminergic agonists such as piribedil, sleep regulators such as melatonin, agents promoting hemostasis, hormones, antitumors, antimigraines, antiparkinsonians, memory promoters, antidepressants, anxiolytics, hypnotics, antidiabetics, antiobesity agents, antifungals or antivirals.

The following examples illustrate the invention but do not limit it in any way.

EXAMPLE 1

The manufacture of the tablets calls for a process known as wet granulation. The preparation of the inner phase is carried out by mixing 320 grams of piribedil with 80 grams of modified, i.e., acetylated, maize starch (Cerestar Top SF12616, company Cerestar) to which 278 grams of calcium dihydrogenphosphate are added. Mixing is carried out using a Turbula for 15 minutes. The mixture obtained is then placed in a second planetary-type mixer and water is progressively added to this mixture with stirring. The mixture is then sieved through a sieve with a mesh size of 1.25 mm. The powder obtained is dried at a temperature of 60° C. for 1 hour and then sieved through a sieve with a mesh size of 0.80 mm. The phase known as the outer phase is produced in parallel. It is composed of the mixture of 150 grams of Gantrez MS 955 and 160 grams of modified maize starch (Cerestar Top SF12616). Mixing is carried out using a Turbula tumbler mixer for 15 minutes. The inner and outer phases are then mixed using a Turbula tumbler mixer. 10 grams of magnesium stearate and 2 grams of colloidal silica are then added to this mixture. The whole is mixed using a Turbula tumbler mixer. The mixture obtained is graded by passing through a sieve with a mesh size of 0.4 mm.

EXAMPLE 2

The manufacture of the tablets calls for a process known as wet granulation. The preparation of the inner phase is carried out by mixing 320 grams of piribedil with 80 grams of modified maize starch (Cerestar Top SF12616) to which 278 grams of lactose (Lactose Fast Flo, company Seppic) are added. Mixing is carried out using a Turbula for 15 minutes. The mixture obtained is then placed in a second tumbler mixer and water is progressively added to this mixture with agitation. The mixture is then sieved through a sieve with a mesh size of 1.25 mm. The powder obtained is dried at a temperature of 60° C. for 1 hour and then sieved through a sieve with a mesh size of 0.80 min. The phase known as the outer phase is prepared in parallel. It is composed of the mixture of 150 grams of Gantrez MS 955 and 160 grams of modified maize starch (Cerestar Top SF12616). Mixing is carried out using a Turbula tumbler mixer for 15 minutes. The inner and outer phases are then mixed using a Turbula tumbler mixer. 10 grams of magnesium stearate and 2 grams of colloidal silica are then added to this mixture. The whole is mixed using a Turbula tumbler mixer. The mixture obtained is graded by passing through a sieve with a mesh size of 0.4 mm.

EXAMPLE 3

The manufacture of the tablets calls for a process known as wet granulation. The preparation of the inner phase is carried out by mixing 166.5 grams of piribedil with 80 grams of modified maize starch (Cerestar Top SF 12616, company Cerestar) to which 373 grams of calcium hydrogenphosphate are added. Mixing is carried out using a tumbler mixer of Ours Varymixer type. 66.5 grams of ethyl acrylate and methyl methacrylate copolymer as a 30% aqueous solution on a dry weight basis are added progressively with agitation. The amount of wetting liquid necessary for wet granulation is obtained by addition of purified water. The mixture obtained is then passed into a Frewitt-type granulator through a 2 mm grid. The mixture obtained is then dried in an extracted oven at 60° C. for two hours. The mixture is then passed into a Frewitt-type granulator through a 0.7 mm grid. The phase known as the outer phase is prepared in parallel. It is composed of the mixture of 160 grams of Gantrez MS 955 (company ISP) and 147 grams of hydroxypropyl methylcellulose (HPMC K 100M P, Colorcon). Mixing of the two phases is carried out in a Rhon-type tumbler mixer. The lubricants are added to this mixture: 5 grams of magnesium stearate and 2 grams of colloidal silica sieved beforehand through 0.4 mm. The whole is mixed in a Rhon-type tumbler mixer. The particle obtained is then compressed.

EXAMPLE 4

According to the same process as Example 1, the 320 grams of piribedil are replaced by 32 grams of melatonin and the amount of calcium dihydrogenphosphate is 566 grams. The remainder is unchanged.

EXAMPLE 5

According to the same process as Example 1, the 320 grams of piribedil are replaced by 32 grams of lidocaine and the amount of calcium dihydrogenphosphate is 566 grams. The remainder is unchanged.

EXAMPLE 6

The manufacture of the tablets calls for a process known as wet granulation. The preparation of the inner phase is carried out by mixing 333 g of amineptine hydrochloride with 79 grams of modified maize starch (Cerestar Top SF 12616, company Cerestar) to which 260 grams of calcium hydrogenphosphate are added. Mixing is carried out using a tumbler mixer of Ours Varymixer type. Water is added progressively with agitation and the mixture is then passed into a Frewitt-type granulator through a 2 mm grid. The powder obtained is then dried in an extracted oven at 60° C. for two hours. The mixture is then passed into a Frewitt-type granulator through a 0.7 mm grid. The phase known as the outer phase is prepared in parallel. It is composed of the mixture of 159 grams of Gantrez MS 955 (company ISP) and 157 grams of hydroxypropyl methylcellulose (HMPC K 100M P, company Colorcon). Mixing the two phases is carried out in a Rhon-type tumbler mixer. The lubricants are added to this mixture: 10 grams of magnesium stearate and 2 grams of colloidal silica sieved beforehand through 0.4 mm. The whole is mixed in a Rhon-type tumbler mixer. The particle obtained is then compressed.

EXAMPLE 7

The manufacture of the tablets calls for a process known as wet granulation. The preparation of the inner phase is carried out by mixing 145 grams of 1,3,7-trimethyl-8-{3-[4-(diethylaminocarbonyl)piperazin-1-yl]prop-1-yl}-3,7-dihydro-1H-purine-2,6-dione hydrochloride (described in Patent EP 149578) with 79.5 grams of modified maize starch (Cerestar Top SF 12616, company Cerestar) to which 346 grams of calcium hydrogenphosphate are added. Mixing is carried out using a tumbler mixer of Ours Varymixer type. Water is added progressively with agitation and the mixture is then passed into a Frewitt-type granulator through a 2 mm grid. The powder obtained is then dried in an extracted oven at 60° C. for 2 hours. The mixture is then passed into a Frewitt-type granulator through a 0.7 mm grid. The phase known as the outer phase is prepared in parallel. It is composed of the mixture of 159 grams of Gantrez MS 955 (company ISP), 262.5 grams of hydroxypropyl methylcellulose (HPMC K 100M P, Colorcon) and 1 gram of sodium saccharinate. Mixing of the two phases is carried out in a Rhon-type tumbler mixer. The lubricants are added to this mixture: 5 grams of magnesium stearate and 2 grams of colloidal silica sieved beforehand through 0.4 mm. The whole is mixed in a Rhon-type tumbler mixer. The particle obtained is then compressed.

EXAMPLE 8

The manufacture of the tablets calls for a process known as direct compression. 46.8 grams of dihydroergotamine mesylate are mixed with 100 grams of microcrystalline cellulose (Avicel PH 102, company Seppic) and 250 grams of lactose (Tablettose Meggle, company SPCI). 100 grams of microcrystalline cellulose and 246.2 grams of lactose are then added to this premix. After mixing, 250 grams of Gantrez MS 955 are added. After mixing, 5 grams of magnesium stearate and 2 grams of colloidal silica are added. The lubricants were sieved beforehand through 0.4 mm. The powder obtained is then compressed.

We claim:

1. A bioadhesive pharmaceutical composition for the controlled release of an active principle locally in the buccal cavity or systemically across a mucous membrane, which comprises:

an active principle, a compound (A) selected from the group consisting of a copolymer formed by the copolymerization of methyl vinyl ether and maleic anhydride, a derivative thereof, and mixtures thereof, a compound (B) which is acetylated maize starch, and therapeutically acceptable excipients, wherein the amount of (A) is between 5 and 85% of the total mass of the composition and wherein the amount of (B) is between 5 and 85% of the total mass of the composition, said composition being wet granulated and compressed into a tablet.

2. The tablet as claimed in claim 1, wherein Compound (A) is in the form of an acid, ester or calcium or sodium salt.

3. The tablet as claimed in claim 1, wherein the active principle is an anti-inflammatory agent or an analgesic, whether possessing local or systemic action, a disinfectant, an enzyme, a coronary vasodilator, an antiasthmatic, an antibiotic, a cardiotonic, a local anesthetic, an antianginal, an antidysrhythmic, an antihypertensive, an antitussive, an expectorant, an antihistamine, a dopaminergic agonist, a sleep regulator, a hemostatic, a hormone, an antitumor agent, an antimigraine, an antiparkinsonian, a memory promoter, an antidepressant, an anxiolytic, a hypnotic, a non-hormonal antidiabetic, an antiobesity agent, an antifungal or an antiviral.

4. The tablet as claimed in claim 1, wherein the excipients are selected from the group consisting of diluents, binders, and lubricants to which can optionally be added a dye, sweeteners, disintegrant, or absorption promoter.

* * * * *

UNITED STATES PATENT AND TRADEMARK OFFICE
CERTIFICATE OF CORRECTION

PATENT NO. : 5,672,356
DATED : Sept. 30, 1997
INVENTOR(S) : I. Rauit, G. Pichon, A. Cuine It is certified that error appears in the above-indentified patent and that said Letters Patent is hereby corrected as shown below:

```
Column 1, line 13:  Delete "a" at the end of the line.
     Page 1, line 6

Column 1, line 14:  Insert the word -- rectal -- at the
     beginning of the line.  Page 1, line 6

Column 6, line 47:  Insert -- flavoring, -- at the end of
     the line.  Page 8, line 2 of Claim 7

Column 6, line 48:  "sweetners," should read
     -- sweetner, --.  Page 8, line 2 of Claim 7,
```

Signed and Sealed this

Twenty-seventh Day of October, 1998

Attest:

BRUCE LEHMAN

*Attesting Officer*    *Commissioner of Patents and Trademarks*